United States Patent [19]

Wakatsuka et al.

[11] 4,313,954
[45] Feb. 2, 1982

[54] 6,9-NITRILO-PROSTAGLANDIN ANALOGUES

[75] Inventors: Hirohisa Wakatsuka; Masaki Hayashi; Yoshitaka Konishi, all of Takatsuki, Japan

[73] Assignee: Ono Pharmaceutical Co. Ltd., Osaka, Japan

[21] Appl. No.: 122,704

[22] Filed: Feb. 19, 1980

[30] Foreign Application Priority Data

Feb. 20, 1979 [JP] Japan ............................ 54-17935

[51] Int. Cl.³ .................... A61K 31/40; C07D 209/52
[52] U.S. Cl. ................... 424/274; 260/326.27; 260/349; 560/121; 562/503
[58] Field of Search ............... 260/326.27; 424/274

[56] References Cited

U.S. PATENT DOCUMENTS

| | | | |
|---|---|---|---|
| 4,097,489 | 6/1978 | Bundy | 260/326.27 |
| 4,151,176 | 4/1979 | Bundy | 260/326.27 |
| 4,161,584 | 7/1979 | Bundy | 260/326.27 |
| 4,211,706 | 7/1980 | Bundy | 260/326.27 |
| 4,234,597 | 11/1980 | Hayashi et al. | 260/326.27 |

*Primary Examiner*—Alton D. Rollins
*Attorney, Agent, or Firm*—Stevens, Davis, Miller & Mosher

[57] ABSTRACT

Prostaglandin I₂ analogues of the general formula

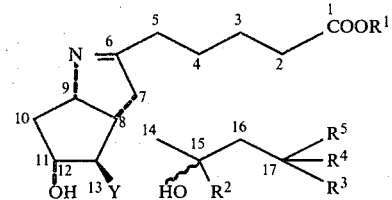

[wherein $R^1$ represents a hydrogen atom, an alkyl group containing from 1 to 12 carbon atoms, an aralkyl group containing from 7 to 13 carbon atoms, a cycloalkyl group containing from 4 to 7 carbon atoms unsubstituted or substituted by at least one alkyl group containing from 1 to 4 carbon atoms, a phenyl group unsubstituted or substituted by at least one halogen atom, trifluoromethyl or phenyl group, or by at least one alkyl, alkoxy or alkylthio group containing from 1 to 4 carbon atoms, or represents a group $-C_mH_{2m}COOR^6$, $-C_nH_{2n}OR^7$ or

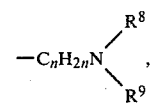

in which m represents an integer of 1 to 12, n represents an integer of 2 to 12, $R^6$, $R^8$ and $R^9$, which may be the same or different, each represent an alkyl group containing from 1 to 4 carbon atoms, and $R^7$ represents a hydrogen atom or an alkyl group containing from 1 to 4 carbon atoms, $R^2$ represents a hydrogen atom or a methyl or ethyl group, $R^3$ represents an alkyl group containing from 1 to 4 carbon atoms, $R^4$ represents a hydrogen atom, or an alkyl group containing from 1 to 4 carbon atoms, $R^5$ represents an alkyl group containing from 1 to 10 carbon atoms, Y represents ethylene or trans-vinylene, the hydroxy group attached to the C-11 carbon atom is in α-configuration, and the wavy line ∿∿∿ attached to the C-15 carbon atom is in α- or β-configuration or a mixture thereof] and non-toxic acid addition salts thereof and, when $R^1$ represents a hydrogen atom, non-toxic salts thereof are new compounds possessing pharmacological properties typical of the prostaglandins.

4 Claims, No Drawings

6,9-NITRILO-PROSTAGLANDIN ANALOGUES

DESCRIPTION

This invention relates to new prostaglandin $I_2$ ($PGI_2$) analogues, to a process for their preparation and to pharmaceutical compositions containing them.

$PGI_2$ (known as prostacyclin) is known as a physiologically active natural substance having the following formula:

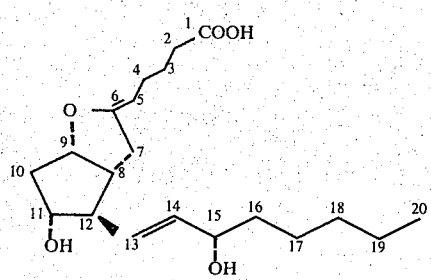

and its chemical name is (5Z,13E)-(9α,11α,15S)-6,9-epoxy-11, 15-dihydroxyprosta-5,13-dienoic acid [cf. Nature, 263, 663 (1976), Prostaglandins, 12, 685 and 915 (1976), ibid, 13, 3 and 375 (1977), and Chemical and Engineering News, Dec. 20, 17 (1976)].

It is well known that $PGI_2$ can be prepared by incubation of prostaglandin $G_2$ ($PGG_2$) or prostaglandin $H_2$ ($PGH_2$) with microsomal fractions prepared from thoracic aorta of swine, mesenteric artery of swine, rabbit aorta or the stomach fundus of rats. $PGI_2$ has a strong relaxing activity on the artery, which is peculiar to the artery and which does not operate on other smooth muscle. Furthermore, $PGI_2$ strongly inhibits arachidonic acid-induced blood platelet aggregation of the human.

Taking into consideration that thromboxane $A_2$ prepared by incubation of $PGG_2$ or $PGH_2$ with blood platelet microsome, has a contracting activity on the artery and an aggregating activity on blood platelets, the properties of $PGI_2$ heretofore mentioned show that $PGI_2$ fulfils a very important physiological part in a living body. $PGI_2$ may be useful in the treatment of arteriosclerosis, cardiac failure or thrombosis.

Widespread investigations have been carried out in order to discover inter alia new products possessing the pharmacological properties of the "natural" $PGI_2$, or one or more of such properties to an enhanced degree, or hitherto unknown pharmacological properties. As a result of extensive research and experimentation it has been discovered that by replacing the 6,9-epoxy group (i.e. —O—) by a group =N—, in which the double bond is attached to the 6-position (hereinafter referred to as a 6,9-nitrilo group), and by introducing either one or two alkyl groups at the C-17 carbon atom, the pharmacological properties of the "natural" $PGI_2$ are, in some aspects of its activities, improved or modified.

The present invention accordingly provides new prostaglandin $I_2$ analogues of the general formula:

[wherein $R^1$ represents a hydrogen atom, an alkyl group containing from 1 to 12 carbon atoms, an aralkyl group containing from 7 to 13 carbon atoms, a cycloalkyl group containing from 4 to 7 carbon atoms unsubstituted or substituted by at least one alkyl group containing from 1 to 4 carbon atoms, a phenyl group unsubstituted or substituted by at least one halogen (preferably chlorine) atom, trifluoromethyl or phenyl group, or by at least one alkyl, alkoxy or alkylthio group containing from 1 to 4 carbon atoms, or represents a group $-C_mH_{2m}COOR^6$, $-C_nH_{2n}OR^7$ or $$-C_nH_{2n}N\begin{matrix}R^8\\ \\R^9\end{matrix},$$

in which m represents an integer of 1 to 12, n represents an integer of 2 to 12, $R^6$, $R^8$ and $R^9$, which may be the same or different, each represent an alkyl group containing from 1 to 4 carbon atoms, and $R^7$ represents a hydrogen atom or an alkyl group containing from 1 to 4 carbon atoms, $R^2$ represents a hydrogen atom, or a methyl or ethyl group, $R^3$ represents an alkyl group containing from 1 to 4 carbon atoms, $R^4$ represents a hydrogen atom, or an alkyl group containing from 1 to 4 carbon atoms, $R^5$ represents an alkyl group containing from 1 to 10 carbon atoms, Y represents ethylene (i.e. $-CH_2CH_2-$), or trans-vinylene (i.e. $\begin{matrix}\diagdown\\H\end{matrix}C=C\begin{matrix}H\\\diagup\end{matrix}$ ), the hydroxy group attached to the C-11 carbon atom is in α-configuration, and the wavy line ⁓ attached to the C-15 carbon atom is in α- or β-configuration (i.e. S- or R-configuration) or a mixture thereof (i.e. RS-configuration)], and non-toxic acid addition salts thereof and, when $R^1$ represents a hydrogen atom, non-toxic salts thereof.

It will be appreciated that acid addition salt formation may take place with the 6,9-nitrilo group; acid addition salt formation is also possible with a group $$-C_nH_{2n}N\begin{matrix}R^8\\ \\R_8^9\end{matrix}$$

within the definition of the symbol $R^1$, in which n, $R^8$ and $R^9$ are as hereinbefore defined.

It is to be understood that alkyl and alkylene groups and alkyl and alkylene moiety of groups referred to in this specification and the accompanying claims may be straight- or branched-chain.

The present invention is concerned with all compounds of general formula II in the optically active "natural" form or its enantiomeric form, or mixtures thereof, more particularly the racemic form, consisting of equimolecular mixtures of the optically active "natural" form and its enantiomeric form.

As will be apparent to those skilled in the art, the compounds depicted in general formula II have at least five centres of chirality, these five centres of chirality being at the C-8, C-9, C-11, C-12 and C-15 carbon atoms. Still further centres of chirality may occur when alkyl or alkylene groups or moieties are branched-chain or at the C-17 carbon atoms. The presence of chirality leads as is well known to the existence of isomerism. However, the compounds of general formula II all have such configuration that the substituent groups attached to the ring carbon atoms in positions identified as 8 and 12 are trans with respect to each other and that the substituent groups attached to the ring carbon atoms in the positions identified as 8 and 9 are cis with respect to each other. Accordingly, all isomers of general formula II, and mixtures thereof, which have those substituent groups attached to the ring carbon atoms in positions 8 and 12 in the trans-configuration, those attached in positions 8 and 9 in the cis-configuration and have hydroxy groups as depicted in the 11- and 15-positions are to be considered within the scope of general formula II.

Examples of the alkyl group containing from 1 to 12 carbon atoms represented by $R^1$ are methyl, ethyl, propyl, butyl, pentyl, hexyl, heptyl, octyl, nonyl, decyl, undecyl, dodecyl, and their isomers.

Examples of the aralkyl group containing from 7 to 13 carbon atoms represented by $R^1$ are benzyl, 1-phenylethyl, 2-phenylethyl, 3-phenylbutyl, 4-phenylbutyl, 1-(2-naphthyl)ethyl, 2-(1-naphthyl)ethyl and biphenylmethyl.

Examples of the cycloalkyl group containing from 4 to 7 carbon atoms unsubstituted or substituted by at least one alkyl group containing from 1 to 4 carbon atoms represented by $R^1$ are cyclobutyl, 1-propylcyclobutyl, 1-butylcyclobutyl, 2-methylcyclobutyl, 2-propylcyclobutyl, 3-ethylcyclobutyl, 3-propylcyclobutyl, 2,3,4-triethylcyclobutyl, cyclopentyl, 3-ethylcyclopentyl, 3-propylcyclopentyl, 3-butylcyclopentyl, 3-tert-butylcyclopentyl, 2,2-dimethylcyclopentyl, (1-methyl-3-propyl)cyclopentyl, (2-methyl-3-propyl)cyclopentyl, (2-methyl-4-propyl)cyclopentyl), cyclohexyl, 3-ethylcyclohexyl, 3-isopropylcyclohexyl, 4-methylcyclohexyl, 4-ethylcyclohexyl, 4-propylcyclohexyl, 4-tert-butylcyclohexyl, 2,2-dimethylcyclohexyl, 2,6-dimethylcyclohexyl, (2,6-dimethyl-4-propyl)cyclohexyl and cycloheptyl.

Examples of the phenyl group unsubstituted or substituted by at least one halogen atom, trifluoromethyl or phenyl group, or alkyl or alkoxy or alkylthio group containing from 1 to 4 carbon atoms represented by $R^1$ are phenyl, 2-, 3- or 4-chlorophenyl, 2,4-dichlorophenyl, 2,4,6-trichlorophenyl, 2-, 3- or 4-tolyl, 2-, 3- or 4-ethylphenyl, 2-, 3- or 4-isopropylphenyl, 2-, 3- or 4-tert-butylphenyl, 4-sec-butylphenyl, 2,4-dimethylphenyl, 2,5-dimethylphenyl, 2,6-dimethylphenyl, 2,6-diethylphenyl, (2-isopropyl-5-methyl)phenyl, 2,6-diisopropylphenyl, (2-tert-butyl-6-methyl)phenyl, (2-tert-butyl-4-methyl)phenyl, 2,4-di-tert-butylphenyl, 2,6-di-tert-butylphenyl, 3,5-di-tert-butylphenyl, 2,4,6-trimethylphenyl, (2-tert-butyl-4,6-dimethyl)phenyl, (2,6-di-tert-butyl-4-methyl)phenyl, 2,4,6-tri-tert-butylphenyl, 3-trifluoromethylphenyl, 4-biphenyl, 2-, 3- or 4-methoxyphenyl, 2-, 3- or 4-ethoxyphenyl, 2-, 3- or 4-methylthiophenyl and 2-, 3- or 4-ethylthiophenyl.

The alkylene group represented by $-C_mH_{2m}-$ and $-C_nH_{2n}-$ may be methylene (when m in the $-C_mH_{2m}-$ moiety is 1), ethylene, trimethylene, tetramethylene, pentamethylene, hexamethylene, heptamethylene, octamethylene, nonamethylene, decamethylene, undecamethylene, dodecamethylene, and their isomers.

The alkyl group containing from 1 to 4 carbon atoms represented by $R^3$, $R^4$, $R^6$, $R^7$, $R^8$ and $R^9$ may be methyl, ethyl, propyl, isopropyl, butyl, isobutyl, sec-butyl and tert-butyl.

Examples of the alkyl group containing from 1 to 10 carbon atoms represented by $R^5$ are methyl, ethyl, propyl, butyl, pentyl, hexyl, heptyl, octyl, nonyl, decyl, and their isomers.

Preferred compounds of general formula II are those wherein $R^1$ represents a hydrogen atom, or an alkyl group containing from 1 to 12 carbon atoms, more preferably from 1 to 4 carbon atoms, especially methyl. Preferably $R^2$ represents a hydrogen atom. Preferably $R^3$ represents a methyl or ethyl group. Preferably $R^4$ represents a hydrogen atom, or a methyl or ethyl group. Preferably $R^5$ represents an ethyl, propyl, butyl or pentyl group. Preferably Y represents a trans-vinylene group. Preferably the hydroxy group attached to the C-15 carbon atom is in α-configuration.

Examples of suitable non-toxic acid addition salts are the salts with inorganic acids, such as hydrochloric acid, hydrobromic acid, hydroiodic acid, sulphuric acid, phosphoric acid and nitric acid, and the salts with organic acids such as acetic acid, propionic acid, lactic acid, tartaric acid, citric acid, benzoic acid, methanesulphonic acid, ethanesulphonic acid, benzenesulphonic acid, toluenesulphonic acid, isethionic acid and succinic acid.

According to a feature of the present invention, the prostaglandin $I_2$ analogues of general formula II, wherein the various symbols are as hereinbefore defined, are prepared by cyclization of a compound of the general formula:

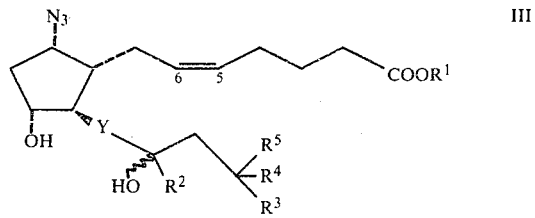

III

[wherein the double bond between $C_5-C_6$ is cis (i.e. Z), and the other symbols are as hereinbefore defined] in an inert organic solvent, e.g. toluene, benzene or acetonitrile, at a temperature from ambient to 110° C.

If desired, the products of general formula II may be purified by conventional means e.g. by thin layer or column chromatography on silica gel, or by recrystallization of acid addition salts of the products (which may be obtained by methods known per se, for example by adding an inorganic or organic acid to the products) to give the pure $PGI_2$ analogues or pharmaceutically-acceptable acid addition salts thereof. By the term "methods known per se" as used in this specification is meant methods heretofore used or described in the chemical literature.

Esters of general formula III, wherein $R^1$ is other than a hydrogen atom, and the other symbols are as hereinbefore defined, may be prepared by esterification of a corresponding acid of general formula III, wherein $R^1$ represents a hydrogen atom, and the other symbols are as hereinbefore defined, by methods known per se. Methods for the esterification are well known, for example, when $R^1$ is an alkyl group, by reaction with (1) a diazoalkane or (2) an N,N-dimethylformamide-dialkyl acetal [cf. Helv. Chim. Acta, 48, 1746 (1965)]; when $R^1$ is an alkyl or aralkyl group, by reaction with (3) an alkyl halide or aralkyl halide; when $R^1$ is an alkyl or aralkyl group or any other esterifying group within the definition of $R^1$, (4) using dicyclohexylcarbodiimide (by the procedure described in our Japanese Pat. No. 762305), (5) using a pivaloyl halide (by the procedure described in our British Pat. No. 1364125, (6) using an arylsulphonyl or alkylsulphonyl halide (by the procedure described in our British Pat. No. 1362956, (7) using isobutyl chloroformate (by the procedure described in British Pat. No. 1492439) or (8) using dipyridyl disulphide and triphenylphosphine [by the procedure described in Tetrahedron Letters, 3409 (1976)].

The preparation of esters using a diazoalkane is carried out by reacting the corresponding acid with an appropriate diazoalkane, e.g. diazomethane, diazobutane or diazodecane, in an inert organic solvent, e.g. diethyl ether, ethyl acetate, methylene chloride, acetone, methanol, or a mixture of two or more of them, at a temperature from ambient to $-10°$ C., preferably at $0°$ C.

The preparation of esters using an N,N-dimethylformamide-dialkylacetal is carried out by reacting the corresponding acid with an N,N-dimethylformamide-dialkyl acetal, e.g. N,N-dimethylformamide-dimethyl acetal, in anhydrous benzene.

The preparation of esters using an alkyl or aralkyl halide is carried out by reacting the corresponding acid with an appropriate alkyl or aralkyl halide, e.g. methyl iodide, butyl bromide, decyl bromide, benzyl chloride or biphenylmethyl bromide, (i) in acetone in the presence of an alkali metal, e.g. sodium or potassium, carbonate [cf. J. Org. Chem., 34, 3717 (1969)], (ii) in N,N-dimethylacetamide or N,N-dimethylformamide in the presence of an alkali metal, e.g. sodium or potassium, bicarbonate [cf. Advan. Org. Chem., 5, 37 (1965)], (iii) in dimethyl sulphoxide in the presence of calcium oxide [cf. Synthesis, 262 (1972)] or (iv) in N,N-dimethylacetamide or N,N-dimethylformamide in the presence of tetramethylammonium hydroxide [cf. Synthetic Comm., 2,215 (1972)] at a temperature of $0°$ C. to ambient.

The preparation of esters using dicyclohexylcarbodiimide is carried out by reacting the corresponding acid with an appropriate alcohol in an inert organic solvent such as a halogenated hydrocarbon, e.g. chloroform or methylene chloride, in the presence of a base such as pyridine or picoline, preferably pyridine, at a temperature of $0°$ C. to ambient.

The preparation of esters using a pivaloyl, arylsulphonyl or alkylsulphonyl halide or isobutyl chloroformate is carried out by reacting the corresponding acid with a tertiary amine, e.g. triethylamine or pyridine, and a pivaloyl halide, e.g. pivaloyl chloride, arylsulphonyl halide, e.g. benzenesulphonyl chloride or p-toluenesulphonyl chloride, alkylsulphonyl halide, e.g. methanesulphonyl chloride or ethanesulphonyl chloride, or isobutyl chloroformate, in the absence or presence of an inert organic solvent such as a halogenated hydrocarbon, e.g. chloroform or methylene chloride, or an ether, e.g. diethyl ether or tetrahydrofuran, to prepare a mixed acid anhydride of the acid, and adding thereto, at a temperature of $0°$ C. to ambient, an alcohol $R^1OH$, wherein $R^1$ is other than a hydrogen atom, to obtain the desired ester.

The preparation of esters using dipyridyl disulphide and triphenylphosphine is carried out by reacting the corresponding acid with an appropriate alcohol in an inert organic solvent, e.g. toluene, benzene or xylene, at a temperature from ambient to $80°$ C.

Compounds of general formula III, wherein $R^1$ represents a hydrogen atom, or an alkyl group containing from 1 to 4 carbon atoms, and the other symbols are as hereinbefore defined, i.e. compounds of the general formula:

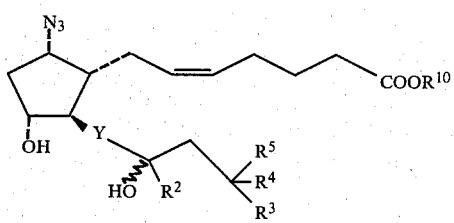

IV (wherein $R^{10}$ represents a hydrogen atom, or an alkyl group containing from 1 to 4 carbon atoms, and the other symbols are as hereinbefore defined) are prepared by converting the group $OR^{11}$ of a compound of the general formula:

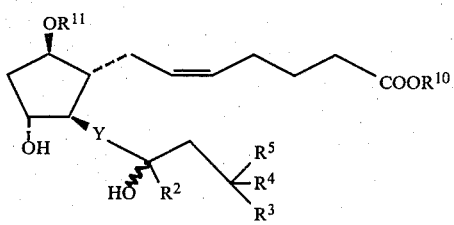

V (wherein $R^{11}$ represents an alkylsulphonyl or arylsulphonyl group, and the other symbols are as hereinbefore defined) by methods known per se into an azido group.

The conversion may be carried out for example by using an azidating reagent such as sodium azide or lithium azide in an inert organic solvent, e.g. hexamethylphosphoramide (HMPA), dimethyl sulphoxide, N,N-dimethylformamide or N,N-dimethylacetamide, at a temperature from ambient to $110°$ C.

Compounds of general formula V may be prepared by the series of reactions depicted schematically below n Scheme A, wherein $R^{12}$ represents a tetrahydropyran-2-yl or tetrahydrofuran-2-yl group, each such group being unsubstituted or substituted by at least one alkyl group, or a 1-ethoxyethyl group, $R^{13}$ represents an alkanoyl group containing from 2 to 5 carbon atoms, or a benzoyl, p-phenylbenzoyl or formyl group, and the other symbols are as hereinbefore defined.

SCHEME A

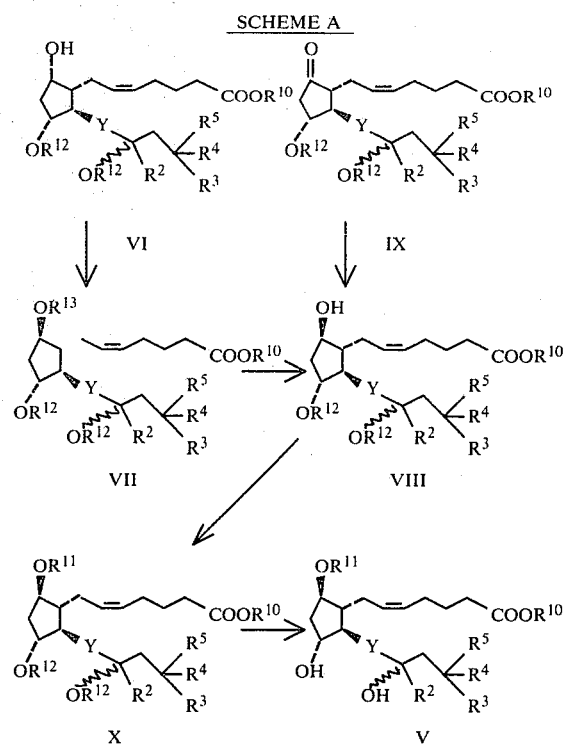

Referring to Scheme A, the conversion of compounds of general formula VI to those of general formula VII may be carried out by using a carboxylic acid $R^{13}OH$, wherein $R^{13}$ is as hereinbefore defined, e.g. formic acid, acetic acid, propionic acid, benzoic acid or p-phenylbenzoic acid, in the presence of a phosphine $(R^{14})_3P$, wherein $R^{14}$ represents an alkyl group containing from 1 to 4 carbon atoms, or a phenyl group unsubstituted or substituted by at least one alkyl group containing from 1 to 4 carbon atoms, e.g. triphenylphosphine or tributylphosphine, and a dialkyl azodicarboxylate $R^{15}OOCN=NCOOR^{15}$, wherein $R^{15}$ represents an alkyl group containing from 1 to 4 carbon atoms, e.g. diethyl azodicarboxylate, in an inert organic solvent, e.g. an ether such as diethyl ether, 1,2-dimethoxyethane, dioxan or tetrahydrofuran, a halogenated hydrocarbon such as methylene chloride or dichloroethane, or a mixture of two or more of them, at a temperature from ambient to 0° C.

The conversion of compounds of general formula VII to those of general formula VIII may be carried out by using an aqueous solution of an alkali metal, e.g. lithium, sodium or potassium, hydroxide or carbonate in the presence of a water-miscible solvent such as an ether, e.g. dioxan or tetrahydrofuran, or an alkanol containing from 1 to 4 carbon atoms, e.g. methanol or ethanol, or by using anhydrous potassium carbonate in an anhydrous alkanol containing from 1 to 4 carbon atoms, e.g. methanol, at a temperature from 0° C. to the reflux temperature of the reaction mixture, preferably at a temperature from 60° C. to ambient.

Compounds of general formula VIII may also be prepared from a compound of general formula IX by methods known per se for the reduction of an oxo group in the 9-position of a prostaglandin E compound to a hydroxy group, for example by means of sodium borohydride in methanol. The product is a mixture of compounds of general formula VIII and those of general formula VI, and the mixture is separated by conventional means, for example by thin layer, column or high-speed liquid chromatography on silica gel to give each isomer.

Compounds of general formula X may be prepared by sulphonylation of a compound of general formula VIII with an alkylsulphonyl halide such as methanesulphonyl chloride or ethanesulphonyl chloride, or an arylsulphonyl halide such as benzenesulphonyl chloride or p-toluenesulphonyl chloride, in an inert organic solvent such as methylene chloride in the presence of a tertiary amine such as triethylamine or pyridine, or in a basic solvent such as pyridine, at a temperature from −30° to 50° C.

The conversion of compounds of general formula X to those of general formula V may be carried out by mild hydrolysis under acidic conditions with (1) an aqueous solution of an organic acid such as acetic acid, propionic acid, oxalic acid, p-toluenesulphonic acid, or of an inorganic acid such as hydrochloric acid, sulphuric acid, phosphoric acid, advantageously, in the presence of an inert organic solvent miscible with water, e.g. a lower alkanol such as methanol or ethanol, preferably methanol, or an ether such as 1,2-dimethoxyethane, dioxan or tetrahydrofuran, preferably tetrahydrofuran, at a temperature from ambient to 75° C., or (2) an anhydrous solution of an organic acid such as p-toluenesulphonic acid or trifluoroacetic acid in a lower alkanol such as methanol or ethanol at a temperature of 0° to 45° C., or (3) an anhydrous solution of p-toluenesulphonic acid-pyridine complex or trifluoroacetic acid-pyridine complex in a lower alkanol such as methanol or ethanol at a temperature of 10° to 60° C. Advantageously the mild hydrolysis under acidic conditions may be carried out with a mixture of dilute hydrochloric acid and tetrahydrofuran, a mixture of dilute hydrochloric acid and methanol, a mixture of acetic acid, water and tetrahydrofuran, a mixture of phosphoric acid, water and tetrahydrofuran, a mixture of p-toluenesulphonic acid and methanol, a mixture of p-toluenesulphonic acid-pyridine complex and methanol or a mixture of trifluoroacetic acid-pyridine complex and methanol.

Starting materials of general formula VI or IX may be prepared by the methods described in the following patent specifications, or obvious modifications thereof: Japanese Pat. Kokai Nos. 49-124048, 49-134656, 50-13362, 50-25549, 50-101340 and 51-68547, British Pat. Nos. 1398291, 1450691 and 1483240, and U.S. Pat. Nos. 3,962,312 and 4,024,174.

Esters of the $PGI_2$ analogues of general formula II, wherein $R^1$ is other than a hydrogen atom and the other symbols are as hereinbefore defined may be prepared by esterification of the corresponding acid of general formula II, wherein $R^1$ represents a hydrogen atom, and the other symbols are as hereinbefore defined, by methods known per se, for example by means heretofore mentioned for the preparation of esters of general formula II, wherein $R^1$ is other than a hydrogen atom and the other symbols are as hereinbefore defined, from the corresponding acids wherein $R^1$ represents a hydrogen atom.

Carboxylic acids of general formula II, wherein $R^1$ represents a hydrogen atom, and the other symbols are as hereinbefore defined, may be prepared by saponification of the corresponding esters of general formula II, wherein $R^1$ is other than a hydrogen atom, and the other symbols are as hereinbefore defined, by methods known per se. For example, methods for the saponification are described in "Compendium of Organic Synthetic Methods", Volume 1 (1971), 2 (1974) or 3 (1977), Section 23, John Wiley & Sons, Inc. (USA); advantageously, the saponification may be effected by using an aqueous solution of an alkali metal, e.g. sodium, potassium or lithium, or an alkaline earth metal, e.g. calcium or barium, hydroxide or carbonate in the absence or presence of a water-miscible solvent such as an ether, e.g. dioxan or tetrahydrofuran, or an alkanol containing from 1 to 4 carbon atoms, e.g. methanol or ethanol, at a temperature of $-10°$ to $100°$ C., preferably at ambient temperature, or using an anhydrous solution of an alkali metal, e.g. sodium, potassium, or lithium, hydroxide or carbonate in an anhydrous alkanol containing from 1 to 4 carbon atoms, e.g. absolute methanol or ethanol, at a temperature of $-10°$ to $100°$ C., preferably at ambient temperature.

Acids of general formula II, wherein $R^1$ represents a hydrogen atom, may, if desired, be converted by methods known per se into salts. Preferably, the salts are non-toxic salts. By the term 'non-toxic salts', as used in this specification, is meant salts the cations (or in the case of acid addition salts referred to hereinafter the anions) of which are relatively innocuous to the animal organism when used in therapeutic doses so that the beneficial pharmacological properties of the compounds of general formula II are not vitiated by side-effects ascribable to those cations (or anions). Preferably the salts are water-soluble. Suitable non-toxic salts include the alkali metal, e.g. sodium or potassium, salts, the alkaline earth metal, e.g. calcium or magnesium, salts and ammonium salts, and pharmaceutically acceptable (i.e. non-toxic) amine salts. Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing 2 or 3 carbon atoms. Suitable non-toxic amine salts are, for example, tetraalkylammonium salts such as tetramethylammonium salts, and other organic amine salts such as methylamine salts, ethylamine salts, isopropylamine salts, tert-butylamine salts, dimethylamine salts, cyclopentylamine salts, benzylamine salts, phenethylamine salts, piperidine salts, monoethanolamine salts, diethanolamine salts, lysine salts and arginine salts.

Salts may be prepared from the acids of general formula II, wherein $R^1$ represents a hydrogen atom, by methods known per se, for example, by reaction of stoichiometric quantities of an acid of general formula II and an appropriate base, e.g. an alkali metal or alkaline earth metal hydroxide or carbonate, ammonium hydroxide, ammonia or an organic amine, in a suitable solvent. The salts may be isolated by lyophilisation of the solution or, if sufficiently insoluble in the reaction medium, by filtration, if necessary after removal of part of the solvent.

The PGI$_2$ analogues of general formula II may, if desired, be converted by methods known per se into acid addition salts, which are preferably non-toxic as hereinbefore defined.

Acid addition salts may be prepared from the compounds of general formula II by methods known per se, for example by reaction of stoichiometric quantities of a compound of general formula II and an appropriate acid, e.g. an inorganic acid such as hydrochloric acid, hydrobromic acid, hydroiodic acid, sulphuric acid, phosphoric acid or nitric acid, or an organic acid such as acetic acid, propionic acid, lactic acid, tartaric acid, citric acid, benzoic acid, methanesulphonic acid, ethanesulphonic acid, benzenesulphonic acid, toluenesulphonic acid, isethionic acid or succinic acid, in a suitable solvent. The acid addition salts may be purified by recrystallisation from a suitable solvent or suitable mixture of two or more solvents.

The PGI$_2$ analogues of general formula II and their non-toxic acid addition salts and, when $R^1$ represents a hydrogen atom, their non-toxic salts, possess the valuable pharmacological properties typical of the prostaglandins in a selective fashion, in particular hypotensive activity, inhibitory activity on blood platelet aggregation, relaxing activity on artery, inhibitory activity on gastric acid secretion and gastric ulceration, and are useful in the treatment of hypertension, in the treatment of disorders of the peripheral circulation, in the prevention and treatment of cerebral thrombosis, myocardial infarction and arteriosclerosis, and in the treatment of gastric ulceration.

For example, in standard laboratory tests, (i) by intravenous administration to the allobarbital-anaesthetized dog, (13E)-(9α,11α,15α,17S)-6,9-nitrilo-11,15-dihydroxy-17,20-dimethylprost-13-enoic acid produces a fall in blood pressure of 42 mm Hg at the dose of 1 μg/kg animal body weight, (ii) (13E)-(9α,11α,15α,17S)-6,9-nitrilo-11,15-dihydroxy-17,20-dimethylprost-13-enoic acid methyl ester produces a 50% inhibition of adenosine diphosphate (ADP)-induced blood platelet aggregation in platelet-rich plasma of rats at the concentration of $7.2 \times 10^{-3}$ μg/ml in comparison with controls, and (iii) in stress ulceration of rats produced by soaking the rats in a water bath at 19° C. for 6 hours after starvation for 24 hours, by oral administration, (13E)-(9α,11α,15α,17S)-6,9-nitrilo-11,15-dihydroxy-17,20-dimethylprost-13-enoic acid produces 58.4% inhibition of stress ulceration at the dose of 500 μg/kg animal body weight.

Preferred PGI$_2$ analogues of the present invention are as follows:

(13E)-(9α,11α,15α)-6,9-nitrilo-11,15-dihydroxy-17-methylprost-13-enoic acid,
(13E)-(9α,11α,15α)-6,9-nitrilo-11,15-dihydroxy-17-ethylprost-13-enoic acid,
(13E)-(9α,11α,15α)-6,9-nitrilo-11,15-dihydroxy-17-propylprost-13-enoic acid,
(13E)-(9α,11α,15α)-6,9-nitrilo-11,15-dihydroxy-17,20-dimethylprost-13-enoic acid,
(13E)-(9α,11α,15α)-6,9-nitrilo-11,15-dihydroxy-17-ethyl-20-methylprost-13-enoic acid,
(13E)-(9α,11α,15α)-6,9-nitrilo-11,15-dihydroxy-17,20-diethylprost-13-enoic acid,
(13E)-(9α,11α,15α)-6,9-nitrilo-11,15-dihydroxy-17-methyl-20-ethylprost-13-enoic acid,
the corresponding 15-methyl and 15-ethyl analogues, and esters, non-toxic salts and non-toxic acid addition salts thereof.

Particularly preferred PGI$_2$ analogues of the present invention are (13E)-(9α,11α,15α)-6,9-nitrilo-11,15-dihydroxy-17,20-dimethylprost-13-enoic acid and its methyl ester and non-toxic salts and acid addition salts thereof; (13E)-(9α,11α,15α,17S)-6,9-nitrilo-11,15-dihydroxy-17,20-dimethylprost-13-enoic acid and non-toxic salts and acid addition salts thereof, and (13E)-(9α,11α,1-5α,17S)-6,9-nitrilo-11,15-dihydroxy-17,20-dimethyl-prost-13-enoic acid methyl ester and non-toxic acid addition salts thereof are more particularly preferred.

The following Reference Examples and Examples illustrate the preparation of compounds of the present invention. In the Reference Examples and Examples, 'TLC', 'IR', 'NMR' and 'MS' represent, respectively, 'Thin layer chromatography', 'Infrared absorption spectrum', 'Nuclear magnetic resonance spectrum', and 'Mass spectrum'. Where solvent ratios are specified in chromatographic separations, the ratios are by volume.

REFERENCE EXAMPLE 1

(5Z,13E)-(9β,11α,15α,17S)-9-Formyloxy-11,15-bis(tetrahydropyran-2-yloxy)-17,20-dimethylprosta-5,13 dienoic acid methyl ester A solution of 1.1 ml of diethyl azodicarboxylate in 5 ml of tetrahydrofuran was added dropwise to a solution of 1.96 g of (5Z,13E)-(9α,11α,15α,17S)-9-hydroxy-11,15-bis(tetrahydropyran-2-yloxy)-17,20-dimethyl-prosta-5,13-dienoic acid methyl ester, 1.84 g of triphenylphosphine and 0.264 ml of formic acid in 30 ml of tetrahydrofuran at −5° C., and the mixture was stirred at −5° C. for one hour, and then at 10° C. for 30 minutes. The reaction mixture was diluted with ethyl acetate, washed with 1 N hydrochloric acid, water, a saturated aqueous solution of sodium bicarbonate, water, and a saturated aqueous solution of sodium chloride, dried over magnesium sulphate, and concentrated under reduced pressure. The residue was purified by column chromatography on silica gel using a mixture of cyclohexane and ethyl acetate (8:1) as eluent to give 1.6 g of the title compound having the following physical characteristic:

TLC (developing solvent, cyclohexane:ethyl acetate=2:1): Rf=0.46.

REFERENCE EXAMPLE 2

(5Z,13E)-(9β,11α,15α,17S)-9-Hydroxy-11,15-bis(tetrahydropyran-2-yloxy)-17,20-dimethylprosta-5,13-dienoic acid methyl ester To a solution of 1.6 g of the formyloxy compound (prepared as described in Reference Example 1) in 15 ml of methanol was added 373 mg of potassium carbonate, and the mixture was stirred at 20° C. for 40 minutes. The reaction mixture was diluted with ethyl acetate, washed with 1 N hydrochloric acid, water, a saturated aqueous solution of sodium bicarbonate, water, and a saturated aqueous solution of sodium chloride, dried over magnesium sulphate, and concentrated under reduced pressure. The residue was purified by column chromatography on silica gel using a mixture of cyclohexane and ethyl acetate (2:1) as eluent to give 1.48 g of the title compound having the following physical characteristics:

TLC (developing solvent, cyclohexane:ethyl acetate=2:1): Rf=0.13;

IR (liquid film): $\nu$=3450, 1740, 1440, 1030, 980 cm$^{-1}$;

NMR (CDCl$_3$ solution): δ=5.40 (4H,m), 4.60(2H,m), 3.60(3H,s), 0.90(6H,m);

MS: m/e=462, 431, 390, 378, 360, 306.

REFERENCE EXAMPLE 3

(5Z,13E)-(9β,11α,15α,17S)-9-(p-Toluenesulphonyloxy)-11,15-bis(tetrahydropyran-2-yloxy)-17,20-dimethyl-prosta-5,13-dienoic acid methyl ester To a solution of 1.16 g of the 9β-hydroxy compound (prepared as described in Reference Example 2) in 3.3 ml of pyridine was added 781 mg of p-toluenesulphonyl chloride, and the mixture was stirred at 30° C. for 21 hours. The reaction mixture was diluted with ethyl acetate, washed with 1 N hydrochloric acid, water, and a saturated aqueous solution of sodium chloride, dried over magnesium sulphate, and concentrated under reduced pressure. The residue was purified by column chromatography on silica gel using a mixture of cyclohexane and ethyl acetate (3:1) as eluent to give 1.46 g of the title compound having the following physical characteristics:

TLC (developing solvent, cyclohexane:ethyl acetate=2:1): Rf=0.46;

IR (liquid film): $\nu$=1740, 1600, 1500, 1440, 1370, 1180, 1025, 980 cm$^{-1}$;

NMR (CDCl$_3$ solution): δ=7.15–7.80(4H,m), 5.00–5.60(4H,m), 4.55(3H,m), 3.60(3H,s), 2.40(3H,s), 0.90(6H,m).

REFERENCE EXAMPLE 4

(5Z,13E)-(9β,11α,15α,17S)-9-(p-Toluenesulphonyloxy)-11,15-dihydroxy-17,20-dimethylprosta-5,13-dienoic acid methyl ester To a solution of 1.46 g of the tetrahydrofuran-2-yloxy compound (prepared as described in Reference Example 3) in 20 ml of methanol was added 53 mg of p-toluenesulphonic acid-pyridine complex, and the mixture was stirred at 50° C. for 1.5 hours. The reaction mixture was diluted with ethyl acetate, washed with water, and a saturated aqueous solution of sodium chloride, dried over magnesium sulphate, and concentrated under reduced pressure. The residue was purified by column chromatography on silica gel using a mixture of cyclohexane and ethyl acetate (1:1) as eluent to give 1.07 g of the title compound having the following physical characteristics:

TLC (developing solvent, cyclohexane:ethyl acetate=1:2): Rf=0.28;

IR (liquid film): $\nu$=3370, 1740, 1600, 1440, 1365, 1180, 1100, 985 cm$^{-1}$;

NMR (CDCl$_3$ solution): δ=7.15–7.80(4H,m), 5.00–5.55(4H,m), 4.55(1H,m), 3.70–4.20(2H,m), 3.60(3H,s), 2.40(3H,s), 0.90(6H,m).

EXAMPLE 1

(5Z,13E)-(9α,11α,15α,17S)-9-Azido-11,15-dihydroxy-17,20-dimethylprosta-5,13-dienoic acid methyl ester To a solution of 1.07 g of the p-toluenesulphonyloxy compound (prepared as described in Reference Example 4) in 15 ml of dimethyl sulphoxide was added 255 mg of sodium azide, and the mixture was stirred at 40° C. for 16 hours. The reaction mixture was diluted with ethyl acetate, washed with water, and a saturated aqueous solution of sodium chloride, dried over magnesium sulphate, and concentrated under reduced pressure. The residue was purified by column chromatography on silica gel using a mixture of cyclohexane and ethyl acetate (1:1) as eluent to give 560 mg of the title compound having the following physical characteristics:

TLC (developing solvent, ethyl acetate:methanol=20:1): Rf=0.55;

IR (liquid film): $\nu$=3360, 2100, 1740, 1440, 1340, 1280, 975 cm$^{-1}$;

NMR (CDCl$_3$ solution): $\delta$=5.15–5.60(4H,m), 3.60(3H,s), 0.90(6H,m);

MS: m/e=393, 375, 364, 362, 360, 350, 294, 293.

EXAMPLE 2

(13E)-(9$\alpha$,11$\alpha$,15$\alpha$,17S)-6,9-Nitrilo-11,15-dihydroxy-17,20-dimethylprost-13-enoic acid methyl ester A solution of 560 mg of the azido compound (prepared as described in Example 1) in 10 ml of toluene was stirred at 65° C. for 15 hours, and the reaction mixture was then concentrated under reduced pressure. The residue was purified by column chromatography on silica gel using ethyl acetate as eluent to give 504 mg of the title compound having the following physical characteristics:

TLC (developing solvent, ethyl acetate:methanol=10:1): Rf=0.14;

IR (liquid film): $\nu$=3350, 1740, 1640, 1440, 1250, 1175 1090, 975 cm$^{-1}$;

NMR (CDCl$_3$ solution): $\delta$=5.47(2H,m), 3.97–4.43(2H,m), 3.55–3.88(1H,m), 3.66(3H,s), 3.41(2H,m), 0.76–1.02(6H,m);

MS: m/e=393, 376, 375, 364, 362, 350, 294, 293.

EXAMPLE 3

(13E)-(9$\alpha$,11$\alpha$,15$\alpha$,17S)-6,9-Nitrilo-11,15-dihydroxy-17,20-dimethylprost-13-enoic acid To a solution of 160 mg of the ester compound (prepared as described in Example 2) in 2.5 ml of methanol was added 0.906 ml of a 0.517 N aqueous solution of sodium hydroxide, and the mixture was stirred at 45° C. for 16 hours. The reaction mixture was concentrated under reduced pressure, the residue was dissolved in 3 ml of water, washed with ethyl acetate, neutralised to pH 7 with 0.47 ml of 1 N hydrochloric acid, and concentrated under reduced pressure. To the residue was added isopropanol, insoluble sodium chloride was filtered off, and the filtrate was concentrated under reduced pressure to give 149 mg of the title compound having the following physical characteristics:

TLC (developing solvent, ethyl acetate:methanol=2:1): Rf=0.13;

IR (CHCl$_3$ solution): $\nu$=3350, 1710, 1640, 1460, 1075, 975 cm$^{-1}$;

NMR (CDCl$_3$ solution): $\delta$=6.69(3H,m), 5.46(2H,m), 4.42(1H,m), 4.09(1H,m), 3.81(1H,m), 0.80–1.00(6H,m);

MS: m/e=379, 361, 350, 336, 318, 306, 293, 280, 252 208, 180.

The present invention includes within its scope pharmaceutical compositions which comprise at least one new therapeutically useful compound of general formula II, or non-toxic acid addition salt thereof or, when R$^1$ represents a hydrogen atom, non-toxic salt thereof, together with a pharmaceutical carrier or coating. In clinical practice, the new compounds of the present invention will normally be administered orally, vaginally, rectally or parenterally.

Solid compositions for oral administration include compressed tablets, pills, dispersible powders and granules. In such solid compositions one or more of the active compounds is, or are, admixed with at least one inert diluent such as calcium carbonate, potato starch, dextrin, alginic acid, lactose, mannitol, glucose or cacao butter. The compositions may also comprise, as is normal practice, additional substances other than inert diluents, e.g. lubricating agents such as magnesium stearate. The tablets or pills may, if desired, be coated and made into sugar-coated, gelatin-coated, enteric-coated or film-coated tablets or pills, or tablets or pills coated with two or more layers.

Liquid compositions for oral administration include pharmaceutically-acceptable emulsions, solutions, suspensions, syrups and elixirs containing inert diluents commonly used in the art, such as water or liquid paraffin. Besides inert diluents such compositions may also comprise adjuvants such as wetting and suspending agents, and sweetening, flavouring, perfuming and preserving agents.

The compositions according to the invention for oral administration, also include capsules of absorbable material such as gelatin containing one or more of the active substances with or without the addition of diluents or excipients.

Solid compositions for intrarectal administration include suppositories formulated in manner known per se and containing one or more of the active compounds.

Solid or ointment compositions for vaginal administration include pessaries, silicone rubber pessaries and ointments formulated in manner known per se and containing one or more of the active compounds with one or more carriers, diluents or supports such as cacao butter, macrogol, Witepsol (registered trade mark), silicone rubber or vaseline.

Preparations according to the invention for parenteral administration include sterile aqueous or non-aqueous solutions, suspensions or emulsions. Examples of non-aqueous solvents or suspending media are propylene glycol, polyethylene glycol, ethanol, vegetable oils such as olive oil, and injectable organic esters such as ethyl oleate and sorbitan esters. These compositions may also include adjuvants such as preserving, wetting, emulsifying and dispersing agents. They may be sterilised, for example by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance.

The dosage employed depends upon the desired therapeutic effect, the route of administration, the duration of the treatment, and the age and body weight of the patient.

In the human adult, each dose per person is generally between 0.05 and 500 $\mu$g by parenteral administration in the treatment of hypertension or disorders of the peripheral circulation, or in the prevention and treatment of cerebral thrombosis, myocardial infarction and arteriosclerosis, or between 0.5 and 1000 $\mu$g by oral administration in the treatment of gastric ulceration.

The following Example illustrates pharmaceutical compositions according to the invention.

EXAMPLE 4

(13E)-(9α,11α,15α,17S)-6,9-Nitrilo-11,15-dihydroxy-17,20-dimethylprost-13-enoic acid (500 μg) was dissolved in ethanol (5 ml). The solution was then sterilised by passage through a bacteria-retaining filter and placed in 0.1 ml portions in 1 ml ampoules, to give 10 μg of (13E)-(9α,11α,15α,17S)-6,9-nitrilo-11,15-dihydroxy-17,20-dimethylprost-13-enoic acid per ampoule. The ampoules were sealed. The contents of an ampoule diluted to a suitable volume, e.g. with 1 ml of tris-HCl-buffer solution (pH 8.6), gave a solution ready for administration by injection.

We claim:

1. A prostaglandin analogue which is (13E)-(9α,1-1α,15α)-6,9-nitrilo-11,15-dihydroxy-17,20-dimethylprost-13-enoic acid and its methyl ester and non-toxic salts and acid addition salts thereof.

2. A prostaglandin analogue which is (13E)-(9α,1-1α,15α,17S)-6,9-nitrilo-11,15-dihydroxy-17,20-dimethylprost-13-enoic acid and non-toxic salts and acid addition salts thereof.

3. A prostaglandin analogue which is (13E)-(9α,1-1α,15α,17S)-6,9-nitrilo-11,15-dihydroxy-17,20-dimethylprost-13-enoic acid methyl ester and non-toxic acid addition salts thereof.

4. A pharmaceutical composition useful in the treatment of hypertension or disorders of the peripheral circulation, or in the prevention and treatment of cerebral thrombosis, myocardial infarction and arteriosclerosis, or in the treatment of gastric ulceration, which comprises as active ingredient an effective amount of at least one prostaglandin analogue selected from the class consisting of (13E)-(9α,11α,15α)-6,9-nitrilo-11,15-dihydroxy-17,20-dimethylprost-13-enoic acid, (13E)-(9α,1-1α,15α, 17S)-6,9-nitrilo-11,15-dihydroxy-17,20-dimethylprost-13-enoic acid, or a non-toxic salt or non-toxic acid addition salt of a said acid, the methyl ester of a said acid or a non-toxic acid addition salt of the methyl ester, in association with a pharmaceutical carrier or coating.

* * * * *